(12) United States Patent
Fitterer et al.

(10) Patent No.: US 12,303,651 B2
(45) Date of Patent: May 20, 2025

(54) FULLY COMPLIANT LARGE BORE EXPANDABLE SHEATH

(71) Applicant: BOSTON SCIENTIFIC SCIMED, INC., Maple Grove, MN (US)

(72) Inventors: Mimi Trinh Fitterer, Belmont, CA (US); Takashi H. Ino, San Jose, CA (US); Randy S. Gamarra, Sunnyvale, CA (US); Floriza Q. Escalona, San Jose, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 985 days.

(21) Appl. No.: 17/160,662

(22) Filed: Jan. 28, 2021

(65) Prior Publication Data
US 2021/0162171 A1 Jun. 3, 2021

Related U.S. Application Data

(63) Continuation of application No. 15/001,682, filed on Jan. 20, 2016, now Pat. No. 10,918,829.
(Continued)

(51) Int. Cl.
*A61M 25/00* (2006.01)
*A61M 25/01* (2006.01)
(Continued)

(52) U.S. Cl.
CPC .... *A61M 25/0045* (2013.01); *A61M 25/0023* (2013.01); *A61M 25/01* (2013.01);
(Continued)

(58) Field of Classification Search
CPC .. B29C 53/08; B29C 66/522; A61M 2207/00; B29L 2031/7542
See application file for complete search history.

(56) References Cited

U.S. PATENT DOCUMENTS 4,531,943 A 7/1985 Van Tassel et al.
4,710,181 A 12/1987 Fuqua
(Continued)

FOREIGN PATENT DOCUMENTS

EP 0177177 A2 4/1986
EP 0249456 A2 12/1987
(Continued)

OTHER PUBLICATIONS

International Search Report and Written Opinion for International Application No. PCT/US2016/016608, dated Apr. 21, 2016.
(Continued)

*Primary Examiner* — Michael M. Robinson
(74) *Attorney, Agent, or Firm* — Seager Tufte & Wickhem, LLP

(57) ABSTRACT

An expandable sheath may include an inelastic compliant membrane having a lumen therethrough, and a discontinuous outer member bonded to the membrane. The membrane may include one or more folds formed therein. At least a portion of the outer member may extend continuously around a circumference of the membrane in a first configuration. The outer member may be configured to separate to a second configuration when subjected to a radially outward force from within the membrane. The outer member may taper from a first diameter adjacent a proximal hub to a second smaller diameter at a distal end. A method of manufacturing an expandable sheath may include forming one or more folds in a compliant membrane, cutting a plurality of apertures through a wall of an outer covering; and laminating the outer covering onto the membrane, wherein the plurality of apertures is disposed over the one or more folds.

12 Claims, 13 Drawing Sheets

Related U.S. Application Data

(60) Provisional application No. 62/106,439, filed on Jan. 22, 2015.

(51) Int. Cl.
*A61M 25/06* (2006.01)
*A61M 29/02* (2006.01)
*B29C 53/08* (2006.01)
*B29C 65/00* (2006.01)
*B29C 65/48* (2006.01)
*B29L 31/00* (2006.01)

(52) U.S. Cl.
CPC ............ *A61M 29/02* (2013.01); *B29C 53/08* (2013.01); *B29C 65/48* (2013.01); *B29C 66/522* (2013.01); *A61M 2025/0024* (2013.01); *A61M 2025/006* (2013.01); *A61M 25/0662* (2013.01); *A61M 25/0668* (2013.01); *A61M 2207/00* (2013.01); *B29L 2031/7542* (2013.01)

(56) References Cited

U.S. PATENT DOCUMENTS

| | | |
|---|---|---|
| 4,716,901 A | 1/1988 | Jackson et al. |
| 4,738,666 A | 4/1988 | Fuqua |
| 4,921,479 A | 5/1990 | Grayzel |
| 5,104,388 A | 4/1992 | Quackenbush |
| 5,158,545 A | 10/1992 | Trudell et al. |
| 5,176,659 A | 1/1993 | Mancini |
| 5,217,468 A | 6/1993 | Clement |
| 5,234,425 A | 8/1993 | Fogarty et al. |
| 5,256,150 A | 10/1993 | Quiachon et al. |
| 5,318,588 A | 6/1994 | Horzewski et al. |
| 5,380,304 A | 1/1995 | Parker |
| 5,489,277 A | 2/1996 | Tolkoff et al. |
| 5,514,091 A | 5/1996 | Yoon |
| 5,514,236 A | 5/1996 | Avellanet et al. |
| 5,702,373 A | 12/1997 | Samson |
| 5,810,776 A | 9/1998 | Bacich et al. |
| 5,827,227 A | 10/1998 | DeLago |
| 5,863,284 A | 1/1999 | Klein |
| 5,895,410 A | 4/1999 | Forber et al. |
| 5,964,730 A | 10/1999 | Williams et al. |
| 5,997,508 A | 12/1999 | Lunn et al. |
| 6,080,141 A | 6/2000 | Castro et al. |
| 6,090,072 A | 7/2000 | Kratoska et al. |
| 6,090,136 A | 7/2000 | McDonald et al. |
| 6,187,000 B1 | 2/2001 | Davison et al. |
| 6,190,357 B1 | 2/2001 | Ferrari et al. |
| 6,197,016 B1 | 3/2001 | Fourkas et al. |
| 6,277,108 B1 | 8/2001 | McBroom et al. |
| 6,358,238 B1 | 3/2002 | Sherry |
| 6,443,979 B1 | 9/2002 | Stalker et al. |
| 6,494,860 B2 | 12/2002 | Rocamora et al. |
| 6,632,236 B2 | 10/2003 | Hogendijk |
| 6,814,715 B2 | 11/2004 | Bonutti et al. |
| 6,899,727 B2 | 5/2005 | Armstrong et al. |
| 6,939,327 B2 | 9/2005 | Hall et al. |
| 7,144,386 B2 | 12/2006 | Korkor et al. |
| 7,226,451 B2 | 6/2007 | Shluzas et al. |
| 7,309,334 B2 | 12/2007 | Von Hoffmann |
| 7,329,268 B2 | 2/2008 | Van Nguyen et al. |
| 7,534,250 B2 | 5/2009 | Schaeffer et al. |
| 7,670,354 B2 | 3/2010 | Davison et al. |
| 7,713,193 B2 | 5/2010 | Nance et al. |
| 7,766,820 B2 | 8/2010 | Core |
| 7,785,360 B2 | 8/2010 | Freitag |
| 7,837,769 B2 | 11/2010 | Lahr |
| 7,879,024 B2 | 2/2011 | Thorstenson et al. |
| 7,892,203 B2 | 2/2011 | Lenker et al. |
| 7,963,952 B2 | 6/2011 | Wright, Jr. et al. |
| 8,092,481 B2 | 1/2012 | Nance et al. |
| 8,317,817 B2 | 11/2012 | Davison et al. |
| 8,690,936 B2 | 4/2014 | Nguyen et al. |
| 8,744,572 B1 | 6/2014 | Greenhut et al. |
| 8,764,704 B2 | 7/2014 | Lenker et al. |
| 9,089,669 B2 | 7/2015 | Haslinger et al. |
| 2002/0032459 A1 | 3/2002 | Horzewski et al. |
| 2004/0006344 A1 | 1/2004 | Nguyen et al. |
| 2004/0087968 A1 | 5/2004 | Core |
| 2005/0085842 A1 | 4/2005 | Eversull et al. |
| 2005/0124937 A1 | 6/2005 | Kick et al. |
| 2005/0216047 A1 | 9/2005 | Kumoyama et al. |
| 2005/0222576 A1 | 10/2005 | Kick et al. |
| 2006/0020321 A1 | 1/2006 | Parker |
| 2006/0135962 A1 | 6/2006 | Kick et al. |
| 2006/0135981 A1 | 6/2006 | Lenker et al. |
| 2006/0217755 A1 | 9/2006 | Eversull et al. |
| 2007/0021768 A1* | 1/2007 | Nance ............... A61M 25/0662 606/192 |
| 2007/0074805 A1 | 4/2007 | Leeflang et al. |
| 2007/0087148 A1 | 4/2007 | Okushi et al. |
| 2008/0004571 A1 | 1/2008 | Voss |
| 2008/0114331 A1 | 5/2008 | Holman et al. |
| 2008/0200943 A1 | 8/2008 | Barker et al. |
| 2008/0243081 A1 | 10/2008 | Nance et al. |
| 2009/0043285 A1 | 2/2009 | Stehr et al. |
| 2010/0094392 A1 | 4/2010 | Nguyen et al. |
| 2013/0079861 A1 | 3/2013 | Reinert et al. |
| 2014/0236122 A1 | 8/2014 | Anderson et al. |

FOREIGN PATENT DOCUMENTS

| | | |
|---|---|---|
| EP | 0385920 A2 | 9/1990 |
| WO | 9219312 A1 | 11/1992 |
| WO | 9307812 A1 | 4/1993 |
| WO | 2003002181 A2 | 1/2003 |
| WO | 2004002562 A2 | 1/2004 |
| WO | 2004037333 A1 | 5/2004 |
| WO | 2005018728 A2 | 3/2005 |
| WO | 2006069215 A2 | 6/2006 |
| WO | 2007035471 A2 | 3/2007 |
| WO | 2008002915 A2 | 1/2008 |
| WO | 2008042311 A1 | 4/2008 |
| WO | 2010017537 A2 | 2/2010 |

OTHER PUBLICATIONS

International Search Report and Written Opinion for International Application No. PCT/US2016/014401, dated Jul. 12, 2016.

* cited by examiner

FULLY COMPLIANT LARGE BORE EXPANDABLE SHEATH

RELATED APPLICATIONS

This application is a continuation of U.S. application Ser. No. 15/001,682, filed Jan. 20, 2016, which claims priority to U.S. Provisional Application No. 62/106,439, filed Jan. 22, 2015. The entirety of these applications is hereby incorporated by reference.

TECHNICAL FIELD

The invention relates generally to medical devices and more particularly to medical devices that are adapted for use in percutaneous medical procedures.

BACKGROUND

Some percutaneous procedures can involve relatively large, bulky medical devices that must be advanced through relatively narrow and tortuous vasculature. Such advancement may result in peripheral damage to the wall of the vessel due to the force exerted by the medical device against the vessel wall. A continuing need exists to reduce or eliminate the chances of injuring the vessel during percutaneous medical procedures.

SUMMARY

In a first aspect, an expandable sheath may include a compliant membrane having a lumen extending therethrough, and a discontinuous outer member bonded to the membrane. At least a portion of the outer member may extend continuously around a circumference of the membrane in a first configuration. The outer member may be configured to separate to a second configuration when subjected to a radially outward force from within the membrane.

In addition or alternatively, and in a second aspect, the membrane is inelastic.

In addition or alternatively, and in a third aspect, the membrane includes one or more folds disposed radially inward of the outer member.

In addition or alternatively, and in a fourth aspect, the one or more folds each form a wave shape.

In addition or alternatively, and in a fifth aspect, the one or more folds each form a T-shape.

In addition or alternatively, and in a sixth aspect, a maximum inner diameter of the lumen increases when the outer member separates.

In addition or alternatively, and in a seventh aspect, the expandable sheath may further comprise an elongate introducer member having a maximum outer diameter less than or equal to a maximum inner diameter of the membrane when the outer member is in the first configuration, the introducer member being configured for insertion into the lumen without separating the outer member.

In addition or alternatively, and in an eighth aspect, the expandable sheath may further comprise an elongate dilator having a maximum outer diameter greater than a maximum inner diameter of the membrane when the outer member is in the first configuration and less than or equal to a maximum inner diameter of the lumen, the dilator being configured to pass through the lumen.

In addition or alternatively, and in a ninth aspect, the outer member is configured to separate from the first configuration to the second configuration upon passage of a medical device through the lumen of the membrane.

In addition or alternatively, and in a tenth aspect, the membrane is non-self-supporting.

In addition or alternatively, and in an eleventh aspect, an expandable sheath may include an inelastic compliant inner membrane laminated to an outer tear-away covering, the inner membrane defining a lumen therethrough having an inner diameter; and a proximal hub. The outer tear-away covering may taper from a first diameter adjacent the proximal hub to a second smaller diameter at a distal end.

In addition or alternatively, and in a twelfth aspect, the inner membrane includes one or more folds disposed radially inward of the outer tear-away covering.

In addition or alternatively, and in a thirteenth aspect, the outer tear-away covering includes a plurality of weakening features disposed over the one or more folds.

In addition or alternatively, and in a fourteenth aspect, the plurality of weakening features is configured to separate when subjected to a radially outward force from within the lumen, thereby permitting the one or more folds to unfold and increase the inner diameter of the lumen.

In addition or alternatively, and in an fifteenth aspect, the expandable sheath may further comprise an elongate introducer member having a maximum outer diameter less than or equal to the inner diameter of the membrane at a location within the outer tear-away covering where the outer tear-away covering is at the first diameter, the introducer member being configured for insertion into the lumen without separating the outer tear-away covering.

In addition or alternatively, and in a sixteenth aspect, a method of manufacturing an expandable sheath may include forming one or more folds in a compliant tubular membrane, thereby reducing an inner diameter of the membrane, wherein the membrane includes a plurality of longitudinal corrugations along an inner surface thereof. The method may include cutting a plurality of apertures through a wall of a tubular outer covering. The method may further include laminating the outer covering onto the membrane, wherein the plurality of apertures is disposed over the one or more folds.

In addition or alternatively, and in a seventeenth aspect, the membrane is inelastic.

In addition or alternatively, and in an eighteenth aspect, the outer covering is configured to separate along the plurality of apertures upon passage of an apparatus having an outer diameter greater than the reduced inner diameter through the membrane.

In addition or alternatively, and in a nineteenth aspect, the membrane is incapable of maintaining an increased inner diameter on its own after removal of the apparatus therefrom.

In addition or alternatively, and in a twentieth aspect, a method of manufacturing an expandable sheath may further include, after laminating the outer covering onto the membrane, attaching a proximal hub to the membrane, the proximal hub including a port in fluid communication with a lumen of the membrane and a hemostatic seal therein.

Although discussed with specific reference to use within the vasculature of a patient, medical devices and methods of use in accordance with the disclosure can be adapted and configured for use in other parts of the anatomy, such as the digestive system, the respiratory system, or other parts of the anatomy of a patient.

Figure 1:
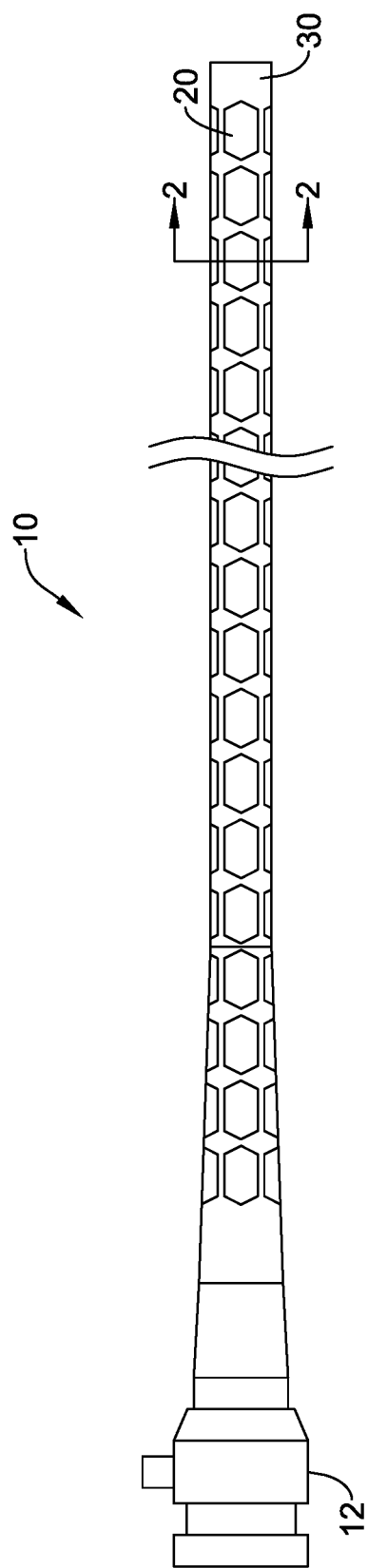
FIG. 1 is a partial schematic view of an example sheath.

While the invention is amenable to various modifications and alternative forms, specifics thereof have been shown by way of example in the drawings and will be described in greater detail below. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For reference, the schematic views shown in FIGS. 1 and 3-9 may generally be described as showing "proximal" toward the left side of the figures and "distal" toward the right side of the figures. Generally speaking, in terms of the orientation of the structural elements relative to each other and the operation of the disclosed device(s), a proximal end may be considered closest to the user (or external to a patient) and a distal end farthest from the user (or internal to a patient). However, the skilled artisan will appreciate that the orientations and/or directions may be reversed as necessary or appropriate.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range, including the endpoints (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional to embodiments or to complement and/or enrich the described embodiment(s), as would be understood by one of ordinary skill in the art.

Some percutaneous medical procedures may require relatively large and/or bulky medical devices (18+ French in size) to be inserted through a patient's vasculature. In some cases, those medical devices may pass through a tortuous and/or peripheral vessel. As the medical device is navigated through the vasculature, the vessel wall may be subjected to a force applied by the medical device as the medical device moves through the vessel lumen and makes contact with the vessel wall. The force may cause injury to the vessel as the medical device is forced to make turns, when the medical device travels through calcified or diseased vessels, and/or if the medical device over expands the vessel.

The risk of injury from the force applied against the vessel wall by a traversing medical device may be reduced by protecting the vessel wall from the force and/or reducing the prominence of features of a delivery sheath which may contact and/or injure the vessel wall. It may also be desirable for a delivery sheath to maintain a smaller profile while permitting expansion to accommodate the passage of a medical device therethrough.

Figure 2A:
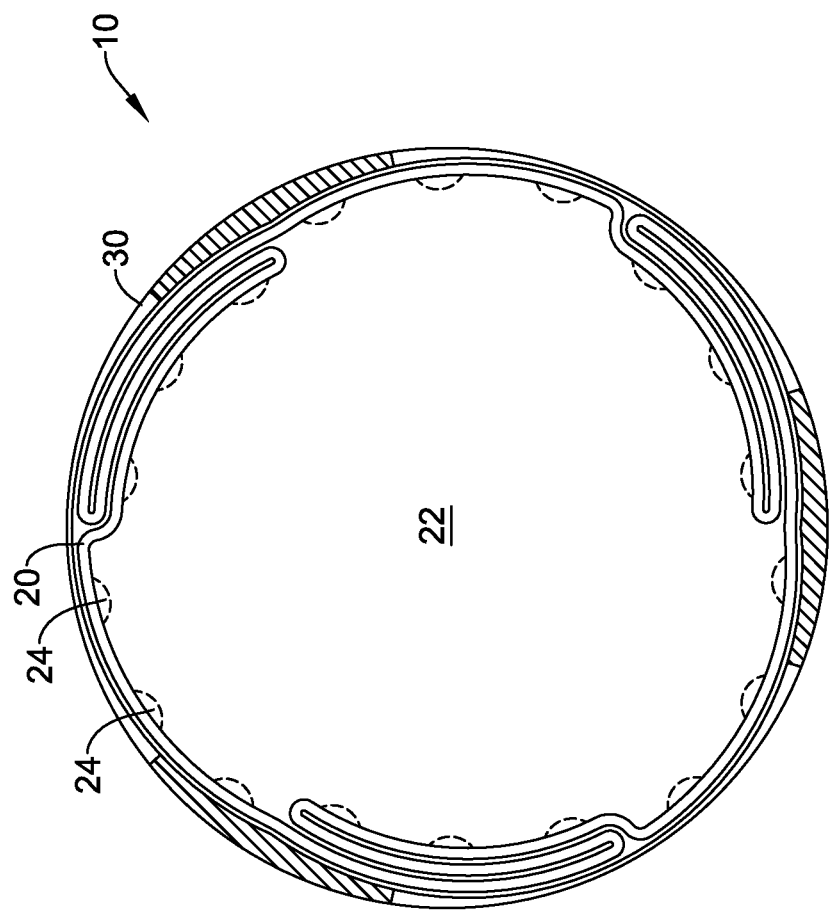
FIG. 2A is a cross-sectional view of an example sheath taken along the line 2-2 of FIG. 1.
Figure 2B:
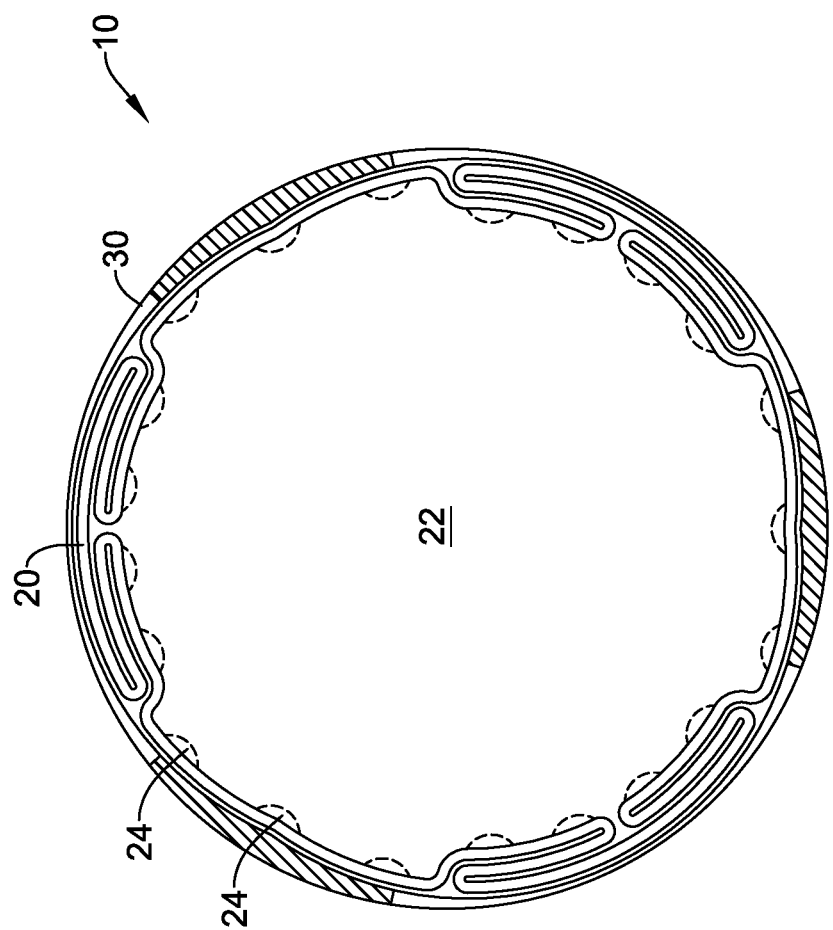
FIG. 2B is a cross-sectional view of an example sheath taken along the line 2-2 of FIG. 1.
Figure 2C:
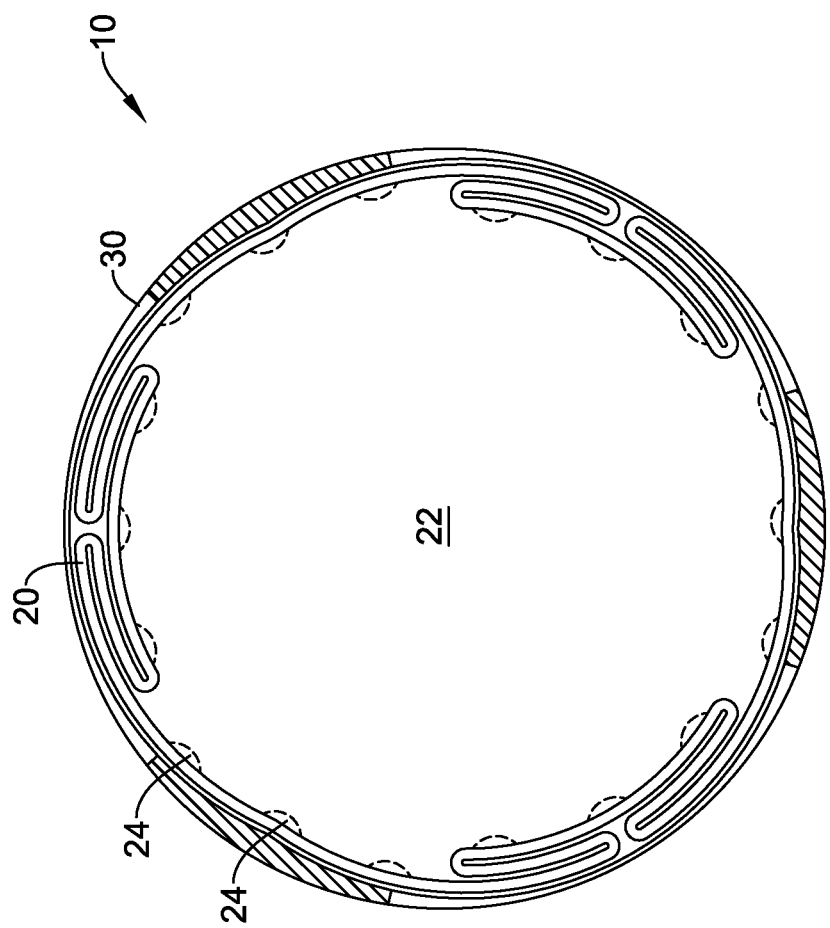
FIG. 2C is a cross-sectional view of an example sheath taken along the line 2-2 of FIG. 1.

FIG. 1 illustrates a schematic view of an example expandable delivery sheath 10, which may include an elongated compliant tubular membrane 20 and a discontinuous outer member or tear-away covering 30 fixedly attached to the membrane 20, as seen for example, in FIGS. 2A-2C. In some embodiments, the membrane 20 may be made from a highly flexible inelastic material, or may have a highly flexible inelastic structure. The membrane 20 is schematically illustrated in the figures as having a substantially annular shape and a lumen 22 extending at least partially therethrough. In some embodiments, the lumen 22 may extend from a proximal end of the membrane 20 to a distal end of the membrane 20. In some embodiments, the lumen 22 may extend completely through an entire length of the membrane 20. However, the skilled artisan will recognize that other shapes and/or configurations are possible within the scope of the present disclosure, as will be apparent from the discussion below, and other shapes or configurations discussed herein may be used in the configuration(s) schematically shown in the figures. An example expandable delivery sheath 10 in accordance with the present disclosure may include none, one, some, or all of the features shown in FIGS. 2A-10.

In general, the membrane 20 may be described as having a compliant elongated tubular structure having a lumen 22 extending therethrough from a proximal end to a distal end. The membrane 20 may include a wall having an inner surface and an outer surface. In some embodiments, a thickness of the wall may be defined by the inner surface and the outer surface.

In some embodiments, the membrane 20 and/or the lumen 22 may be configured to radially expand from a delivery configuration and an expanded configuration when subjected to a radially outward force from within the lumen 22 and/or the membrane 20. In at least some embodiments, the membrane 20 may be substantially or completely compliant, and/or the membrane 20 may have no radial self-bias—that is, no radially inward self-bias and/or no radially outward self-bias. In other words, the membrane 20 may be non-self-supporting and may include no means or mechanism to radially expand and/or open on its own (i.e., absent a radially outward force exerted upon the membrane 20). Instead, the membrane 20 may require a device or object that has a greater outer diameter than an inner diameter of the lumen 22 and/or membrane 20 to be disposed within the lumen 22 to push and/or force the membrane 20 radially outward toward the expanded configuration.

Additionally, the membrane 20 may not require a radially inward force be applied to the membrane 20 to collapse the membrane 20 inward when there is no device, object, etc. disposed within the lumen 22. In other words, the membrane 20 may not be held open or maintain a particular expanded size on its own, or the membrane 20 may be non-self-supporting as mentioned above. Similarly, the membrane 20 may not be biased to collapse inwardly on its own. In other words, the membrane 20 may take the shape and/or form of surrounding tissue(s) after being expanded. For example, a constriction in or of a vessel or body lumen in which the membrane 20 is disposed may urge the membrane 20 radially inward, but the membrane 20 is not self-biased inwardly on its own (i.e., the membrane 20 may have zero return force after expanding/opening).

In the delivery configuration, the lumen 22 may have a first inner diameter defined by the inner surface of the wall. In some embodiments, as will be apparent herein, the first inner diameter may instead be defined as a first inner radial extent and/or distance from a central longitudinal axis of the membrane 20 and/or the expandable delivery sheath 10. In the expanded configuration, the lumen 22 may have a second inner diameter defined by the inner surface of the wall. In some embodiments, as will be apparent herein, the second inner diameter may instead be defined as a second inner radial extent and/or distance from a central longitudinal axis of the membrane 20 and/or the expandable delivery sheath 10. In some embodiments, the second inner diameter may be greater than the first inner diameter. Similarly, the second inner radial extent may be greater than the first inner radial extent.

Similarly, the membrane 20 may have an outer diameter and/or outer radial extent defined by the outer surface of the wall. In the delivery configuration, the membrane 20 may have a first outer diameter and/or first outer radial extent defined by the outer surface of the wall. In the expanded configuration, the membrane 20 may have a second outer diameter and/or a second outer radial extent defined by the outer surface of the wall. In some embodiments, the second outer diameter may be greater than the first outer diameter. Similarly, the second outer radial extent may be greater than the first outer radial extent.

In some embodiments, the membrane 20 may include one or more folds formed therein in the delivery configuration. In some embodiments, the one or more folds may include two folds, three folds, four folds, five folds, six folds, seven folds, eight folds, nine folds, ten folds, or another appropriate number or quantity of folds. In at least some embodiments, the membrane 20 may be disposed radially inward of the outer member or tear-away covering 30. In some embodiments, the one or more folds may each fold back on themselves to form, for example, a wave shape, an S-shape, and/or a Z-shape when viewed in cross-section, such as in FIG. 2A. In some embodiments, the one or more folds may form a T-shape when viewed in cross-section, such as in FIGS. 2B and 2C. In some embodiments, each of the one or more folds forming a T-shape may include two or more distinct wave, S-shaped, or Z-shaped secondary folds within and thus forming each of the one or more T-shaped folds. Other shapes and configurations, while not expressly illustrated, are also contemplated.

In some embodiments, the outer member or tear-away covering 30 may be fixedly attached to the outer surface of the wall of the membrane 20. In some embodiments, the outer member or tear-away covering 30 may be bonded, laminated, fused, glued, co-molded, melted, welded, or other suitable means, to the outer surface of the wall of the membrane 20. In other words, in some embodiments, the outer member or tear-away covering 30 may be permanently attached to the outer surface of the membrane 20. In some embodiments, the outer member or tear-away covering 30 may be formed from a polymeric material, which may form at least a portion of a wall of the outer member or tear-away covering 30. In some embodiments, the outer member or tear-away covering 30 may be formed from the same material as the membrane 20. In some embodiments, the outer member or tear-away covering 30 may be formed from a different material than the membrane 20. In some embodiments, some or all of the outer member or tear-away covering 30 may be fixedly attached to the outer surface of the wall of the membrane 20. In some embodiments, the entire outer member or tear-away covering 30 may be fixedly attached to the outer surface of the wall of the membrane 20.

In some embodiments, at least a portion of the outer member or tear-away covering 30 may extend continuously around a circumference of the membrane 20 in a first configuration. In some embodiments, at least a portion of the outer member or tear-away covering 30 may be discontinuous. In other words, in some embodiments, the outer member or tear-away covering 30 may include a plurality of openings, cutouts, perforations, notches, holes, apertures, or other weakening features formed in the wall of the outer member or tear-away covering 30 which effectively remove at least (or in some cases, only) a portion of the wall of the outer member or tear-away covering 30. In some embodiments, the plurality of openings, cutouts, perforations, notches, holes, apertures, or other weakening features formed in the wall of the outer member or tear-away covering 30 may be arranged in one or more longitudinal lines along the length of the expandable delivery sheath 10, the membrane 20, and/or the outer member or tear-away covering 30. In some embodiments, the plurality of openings, cutouts, perforations, notches, holes, apertures, or other weakening features formed in the wall of the outer member or tear-away covering 30 may extend laterally and/or transversely through the wall of the outer member or tear-away covering 30 relative to the central longitudinal axis. In some embodiments, a wall thickness of the outer member or tear-away covering may be tapered about the circumference of the membrane 20 such that a reduced thickness region of the outer member or tear-away covering 30 is disposed adjacent to, radially outward of, in communication with, and/or directly over the one or more folds of the membrane 20.

Figure 6:
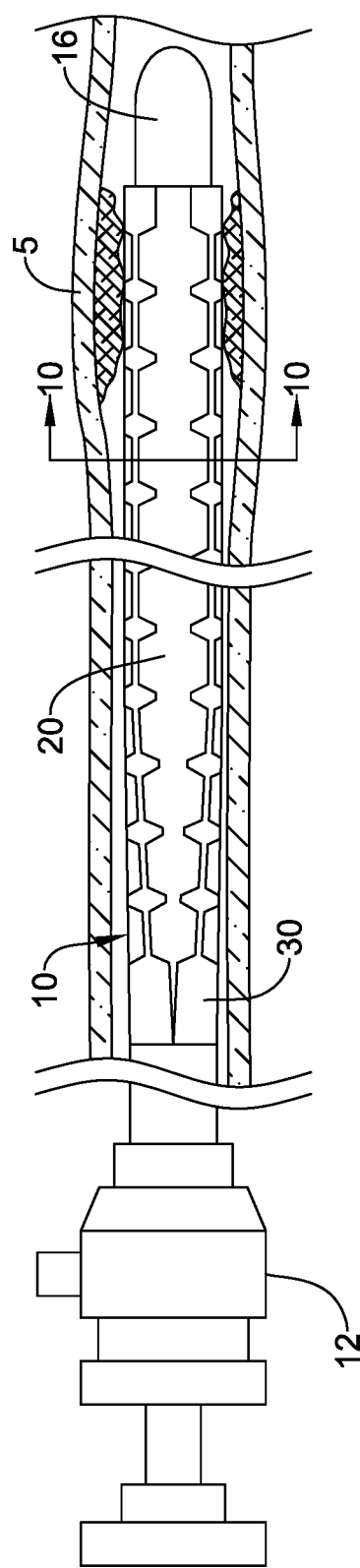
FIG. 6 illustrates an example sheath expanded within a vessel by an example dilator.
Figure 8:
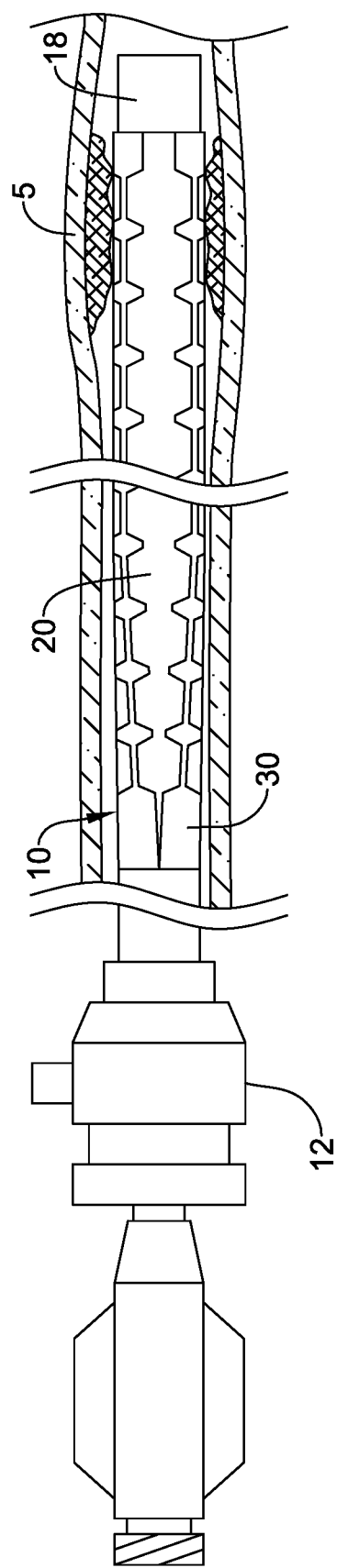
FIG. 8 illustrates an example medical device being inserted through a pre-expanded example sheath.
Figure 8A:
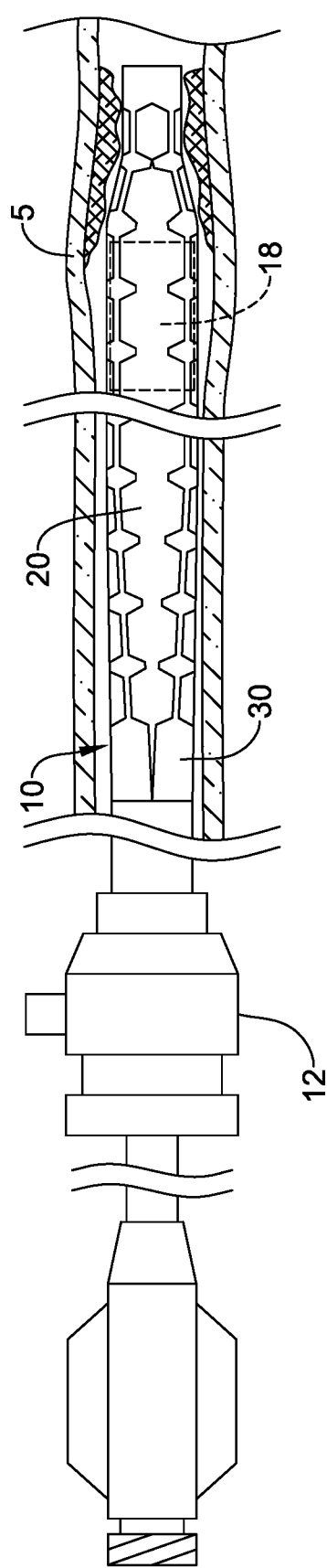
FIG. 8A illustrates an example medical device expanding an example sheath as the medical device is inserted through the sheath.

In some embodiments, the outer member or tear-away covering 30 is configured to separate, split, or tear to a second configuration when subjected to a radially outward force from within the membrane 20 to permit the membrane 20 to transition toward and/or radially expand to the expanded configuration, as seen in FIGS. 6 and 8A. In some embodiments, the outer member or tear-away covering 30 may be configured to separate, split, or tear along and/or through the plurality of openings, cutouts, perforations, notches, holes, apertures, or other weakening features formed in the wall of the outer member or tear-away covering 30. In other words, the outer member or tear-away covering 30 may separate, split, or tear where the outer member or tear-away covering 30 is discontinuous. In some embodiments, when the outer member or tear-away covering 30 separates to the second configuration, the membrane 20 may expand radially outward toward the expanded configuration, and the lumen 22 may expand from the first inner diameter and/or the first inner radial extent to the second inner diameter and/or the second inner radial extent.

In at least some embodiments, the plurality of openings, cutouts, perforations, notches, holes, apertures, or other weakening features formed in the wall of the outer member or tear-away covering 30 may be positioned adjacent to, radially outward of, in communication with, and/or directly over the one or more folds formed in the membrane 20. As mentioned above, in some embodiments, the plurality of openings, cutouts, perforations, notches, holes, apertures, or other weakening features formed in the wall of the outer member or tear-away covering 30 may be arranged in one or more longitudinal lines along the length of the expandable delivery sheath 10, the membrane 20, and/or the outer member or tear-away covering 30. Accordingly, in some embodiments, the plurality of openings, cutouts, perforations, notches, holes, apertures, or other weakening features formed in the wall of the outer member or tear-away covering 30 may be arranged in one or more longitudinal lines adjacent to, radially outward of, in communication with, and/or directly over the one or more folds and/or the two or more secondary folds formed in the membrane 20. In some embodiments, the one or more longitudinal lines may directly correspond to the one or more folds and/or the two or more secondary folds. In some embodiments, there may be more longitudinal lines than folds and/or secondary folds (i.e., 2 folds with 3 or more lines of openings, cutouts, etc., 3 folds with 4 or more lines of openings, cutouts, etc.). In some embodiments, the reduced thickness region and/or a thinnest thickness of the outer member or tear-away covering 30 may be disposed adjacent to, radially outward of, in communication with, and/or directly over the one or more folds and/or the two or more secondary folds of the membrane 20.

In some embodiments, the membrane 20 may be configured to permit the lumen 22 to radially expand from the first inner diameter and/or the first inner radial extent to the second inner diameter and/or the second inner radial extent. In some embodiments, the membrane 20 is configured to substantially prevent axial stretching along the lumen 22. In other words, the membrane 20 may permit the lumen 22 to expand radially outward from a central longitudinal axis of the membrane 20 and/or the expandable delivery sheath 10 without stretching or expanding in an axial or longitudinal direction. In some embodiments, the second inner diameter and/or the second inner radial extent may be greater than the first outer diameter and/or the first outer radial extent. In some embodiments, for example, the first outer radial extent may be about 10 F, 12 F, 14 F, etc. and the second outer inner extent may be about 18 F, 20 F, 22 F, etc. Since the membrane 20 may be made from an inelastic material, the membrane may be configured to expand radially outward to a predetermined maximum second inner diameter and/or second inner radial extent, but may not stretch or expand radially outward beyond the predetermined maximum second inner diameter and/or second inner radial extent.

In some embodiments, for example, as illustrated in FIGS. 2A-2C, a membrane 20 may be formed to include a plurality of corrugations 24 oriented longitudinally, axially, and/or generally parallel to the lumen 22 or a central longitudinal axis of the lumen 22 and/or the membrane 20. In some embodiments, the plurality of corrugations 24 may each be longitudinally aligned with the lumen 22 and/or the central longitudinal axis of the lumen 22 and/or the membrane 20. In some embodiments, the plurality of corrugations 24 may be embedded within the wall of the membrane 20. Although not expressly illustrated, in some embodiments, the plurality of corrugations 24 may be disposed on and/or extend inwardly from the inner surface of the wall of the membrane 20. In some embodiments, the plurality of corrugations 24 may exhibit high non-compliance in an axial direction relative to the central longitudinal axis of the lumen 22.

In some embodiments, the plurality of corrugations 24 may include two, three, four, five, six, seven, eight, ten, twelve, fifteen, or more individual corrugations. In some embodiments, the plurality of corrugations 24 may be spaced or arranged equally and/or symmetrically about an inner circumference and/or the inner surface of the wall of the membrane 20 (i.e., angularly equidistant about the central longitudinal axis). In some embodiments, the plurality of corrugations 24 may be spaced or arranged unequally and/or asymmetrically about an inner circumference and/or the inner surface of the wall of the membrane 20 (i.e., not angularly equidistant about the central longitudinal axis). In some embodiments, the plurality of corrugations 24 may be formed in a suitable shape or cross-section, including but not limited to, round, rectangular, square, triangular, tubular, ovoid, other polygonal shapes, or other suitable shapes or cross-sections. In some embodiments, the plurality of corrugations 24 may ease and/or enhance passage of an introducer member 14, a dilator 16, and/or a medical device 18 through the lumen 22 of the membrane 20.

In some embodiments, the inner surface of the wall of the membrane 20 may include one or more layers or coatings, such as a lubricious coating, a hydrophilic coating, a hydrophobic coating, or other suitable coatings, and the like, or the membrane 20 may include a lubricant disposed within the lumen 22. In some embodiments, an outer surface of the expandable delivery sheath 10 and/or the outer member or tear-away covering 30 may include one or more layers or coatings, such as a lubricious coating, a hydrophilic coating, a hydrophobic coating, or other suitable coating, and the like, or the expandable delivery sheath 10 and/or the outer member or tear-away covering 30 may include a lubricant disposed upon the outer surface thereof.

In some embodiments, the plurality of corrugations 24 may be formed with a height (i.e., a distance from the inner surface to an innermost radial extent of the plurality of corrugations and/or membrane 20 from the central longitudinal axis) of about 0.0002 inches up to about 40%, about 50%, about 60%, about 75%, about 85%, or about 95% of a total thickness of the wall.

In some embodiments, the expandable delivery sheath 10 may also include a hemostatic valve or seal disposed within a hub 12 of the expandable delivery sheath 10 at a proximal end of the expandable delivery sheath 10. The hemostatic valve or seal may prevent blood or other bodily fluid(s) from flowing proximally through the lumen 22 of the membrane 20. In at least some embodiments, the hub 12 may include a port in fluid communication with the lumen 22 of the membrane 20.

In some embodiments, the example expandable delivery sheath 10 may be disposed about or inserted over a guidewire (not shown), although the guidewire is not required. In some embodiments, the expandable delivery sheath 10 and/or the membrane 20 may include a proximal non-expandable section and a distal expandable section. In embodiments having a proximal non-expandable section, the proximal non-expandable section may have an inner diameter or extent sufficient to accept a medical device passing therethrough, while the distal expandable section may have an inner diameter or radial extent in a relaxed condition that is less than a maximum outer diameter or extent of the medical device. The expandable delivery sheath 10 and/or the membrane 20 may be formed using any of the techniques or structures discussed herein. As shown, in some embodiments, the proximal non-expandable section may taper inward toward the distal expandable section at a central tapered section. The central tapered section may provide a transition zone from the proximal non-expandable section to the distal expandable section. The central tapered section may be more expandable at a distal end thereof and less expandable at a proximal end thereof with a linear or non-linear transition therebetween.

In some embodiments, the outer member or tear-away covering 30 may extend from the central tapered section distally to and/or adjacent to the distal end of the expandable delivery sheath 10 and/or the membrane 20.

Figure 3:
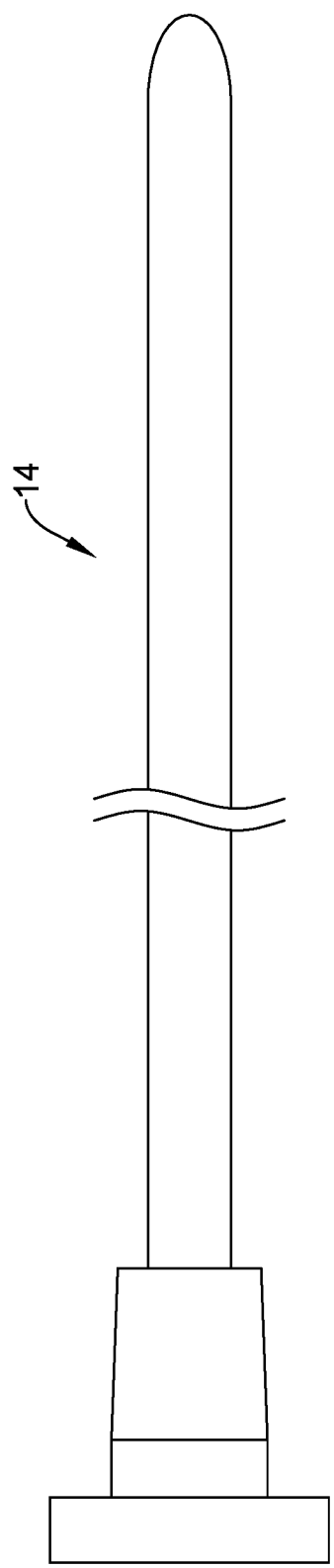
FIG. 3 is a side view of an example insertion device.

FIG. 3 schematically illustrates an elongate introducer member 14. In some embodiments, the introducer member 14 may having a maximum outer diameter and/or maximum outer extent less than or equal to the first inner diameter and/or the first radial inner extent of the membrane 20 when the outer member or tear-away covering 30 is in the first configuration. In at least some embodiments, the introducer member 14 may be configured for insertion into the lumen 22 of the membrane 20 without separating the outer member or tear-away covering 30. In other words, the introducer member 14 may be inserted into the expandable delivery sheath 10 and/or the lumen 22 as a guide member for inserting the expandable delivery sheath 10 into a body lumen of a patient. In some embodiments, the introducer member 14 may be stiffer and/or more rigid than the expandable delivery sheath 10, but may have sufficient flexibility to be navigated to a target area or site. In some embodiments, the introducer member 14 may include a lumen extending longitudinally therethrough, the lumen being sized and configured to slidably accommodate a guide wire or other device therein.

Figure 4:
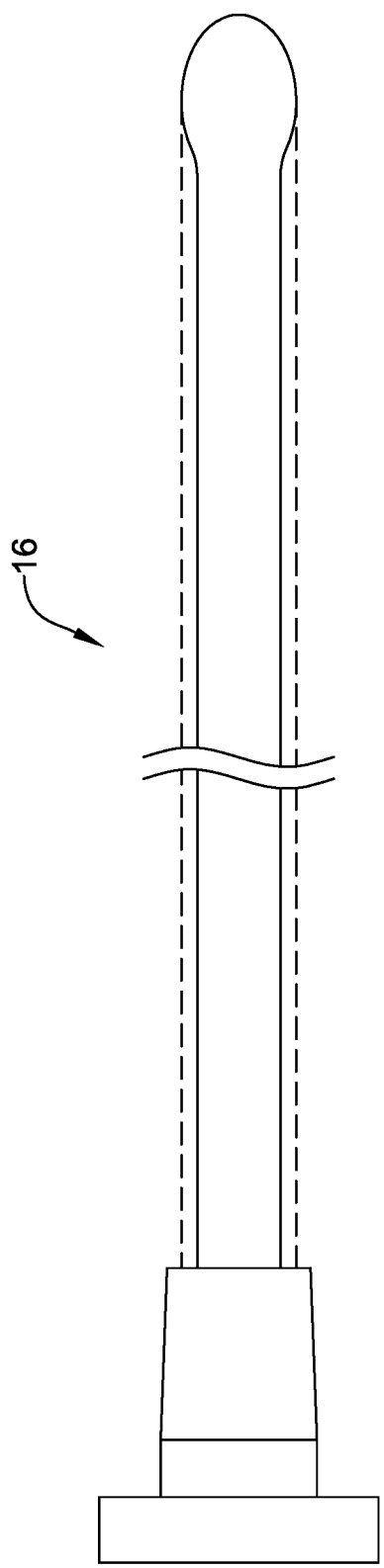
FIG. 4 is a side view of an example dilator.

FIG. 4 schematically illustrates an elongate dilator 16. In some embodiments, the dilator 16 may have a maximum outer diameter and/or maximum outer extent greater than the first inner diameter and/or the first radial inner extent of the lumen 22 and/or the membrane 20 when the outer member or tear-away covering 30 is in the first configuration and less than or equal to the second inner diameter and/or the second radial inner extent of the lumen 22 and/or the membrane 20. In some embodiments, the dilator 16 may include a bulbous distal tip defining the maximum outer diameter or maximum outer extent and a narrower or reduced cross-section shaft portion extending from a proximal end of the dilator 16 to the bulbous distal tip. In some embodiments, the dilator 16 may include a substantially constant outer diameter shaft portion extending from a proximal end of the dilator 16 to a distal end of the dilator 16, wherein the shaft portion defines the maximum outer diameter and/or the maximum outer extent. In some embodiments, the dilator 16 may be configured to be slidably received within and/or pass through the lumen 22 of the membrane 20.

In some embodiments, the outer member or tear-away covering 30 may be configured to separate, split, or tear along and/or through the plurality of openings, cutouts, perforations, notches, holes, apertures, or other weakening features formed in the wall of the outer member or tear-away covering 30 from the first configuration to the second configuration upon passage of the dilator 16 and/or a medical device 18, described in more detail below, through the lumen 22 of the membrane 20. In such embodiments, the increased size of the dilator 16 and/or the medical device 18 relative to the lumen 22 and/or the outer member or tear-away covering 30 may provide the radially outward force from within the lumen 22 of the membrane 20 required to separate the outer member or tear-away covering 30 from the first configuration to the second configuration.

In some embodiments, such as seen in FIG. 1, the expandable delivery sheath 10 and/or the outer member or tear-away covering 30 may include a proximal section adjacent the hub 12, a central tapered section, and a distal section. In some embodiments, the proximal section may define a first outer diameter of the outer member or tear-away covering 30. In some embodiments, the proximal section may be non-expandable. In some embodiments, the distal section may define a second smaller outer diameter at a distal end thereof in a first configuration of the outer member or tear-away covering 30. In some embodiments, the central tapered section may taper from the first outer diameter to the second smaller outer diameter when the outer member or tear-away covering 30 is in the first configuration. In some embodiments, the outer member or tear-away covering 30 may have a substantially constant second outer diameter along the distal section, the central tapered section tapering from the first outer diameter at a distal end of the proximal section to the second smaller outer diameter at a proximal end of the distal section.

Figure 5:
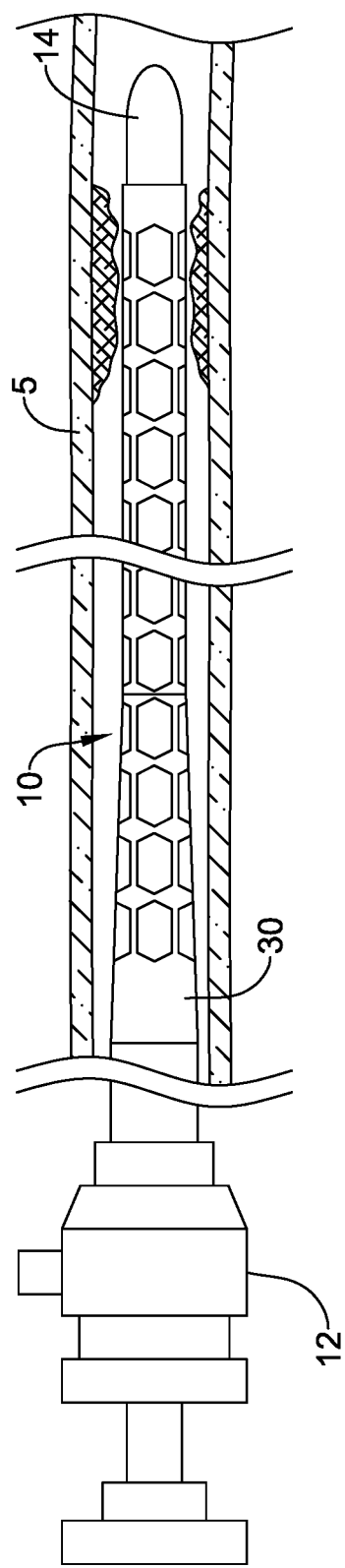
FIG. 5 illustrates an example sheath being inserted into a vessel.

A method of use of an expandable delivery sheath 10 in accordance with the disclosure may be seen, for example, in FIGS. 5-9. In some embodiments, an elongate introducer member 14 may be slidably inserted into and/or received within an expandable delivery sheath 10, which may be constructed and/or formed as described above, for example. As seen in FIG. 5, the introducer member 14 and the expandable delivery sheath 10 may be inserted into and/or navigated within a vessel or body lumen 5 to a target site or area of interest. In some embodiments, the vessel or body lumen 5 may include a partial or total occlusion or obstruction formed therein. Importantly, the disclosed expandable delivery sheath 10 may be used in a vessel or body lumen 5 that does not include a partial or total occlusion therein. As such, the partial occlusion illustrated is merely an example and is not a requirement.

After navigating the expandable delivery sheath 10 to the target site or area of interest, the introducer member 14 may be withdrawn from the expandable delivery sheath 10, while the expandable delivery sheath 10 is maintained within the vessel or body lumen 5 in a substantially constant position. An elongate dilator 16 may be inserted into the lumen 22 of the membrane 20 and advanced distally toward the distal end of the expandable delivery sheath 10, the membrane 20, and/or the outer member or tear-away covering 30. As the dilator 16 reaches, encounters, and/or engages the central tapered section (and later the distal section), the dilator 16 may exert a radially outward force from within the lumen 22 upon the wall of the membrane 20 and/or the outer member or tear-away covering 30. The radially outward force may cause the outer member or tear-away covering 30 to separate, split, or tear along and/or through the plurality of openings, cutouts, perforations, notches, holes, apertures, or other weakening features formed in the wall of the outer member or tear-away covering 30 as the dilator 16 is advanced distally through the lumen 22 of the membrane 20, as seen in FIG. 6. As the outer member or tear-away covering 30 separates, splits, or tears apart, the one or more folds of the membrane 20 are permitted to unfold and increase the inner diameter of the lumen 22. In a vessel or body lumen 5 having a partial or total occlusion, when the dilator 16 is advanced through the occlusion and/or the outer member or tear-away covering 30 is opened/expanded within the occlusion, as seen in FIG. 6 for example, the vessel or body lumen 5 may be deformed or distended by the rigidity of the dilator 16 moving the occlusive material radially outward.

Figure 7:
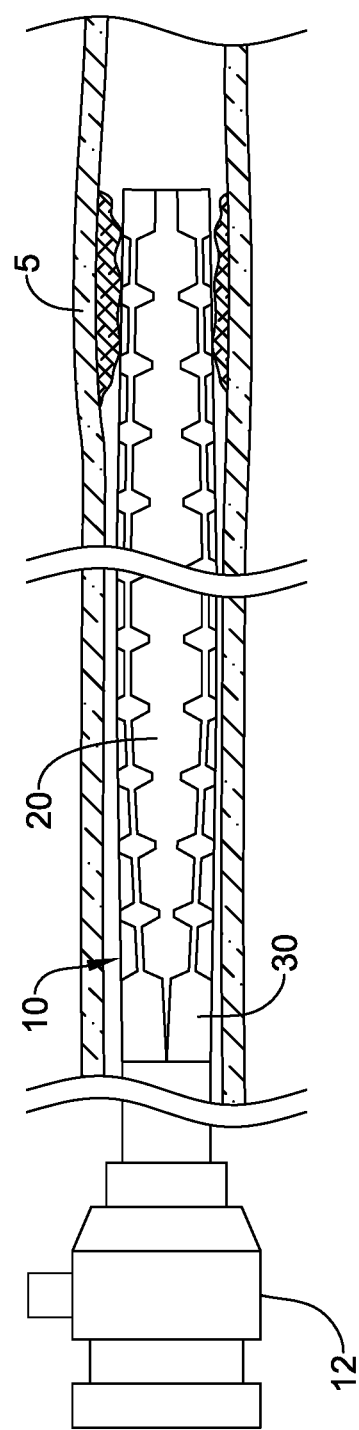
FIG. 7 illustrates an example sheath disposed within a vessel after expansion.

FIG. 7 illustrates the expandable delivery sheath 10 disposed within a vessel or body lumen 5 after the dilator 16 has been withdrawn and/or removed from the lumen 22 of the membrane 20. As described above, the membrane 20 may be compliant with no radial bias of its own. As such, in an example where the vessel or body lumen 5 includes a partial or total occlusion, when the radially outward force provided by the dilator 16 is removed, the vessel or body lumen 5 may, in some instances, rebound radially inward such that the occlusive material partially collapses the membrane 20 radially inward as the vessel or body lumen 5 returns to a normal or equilibrium position or configuration. Since the membrane 20 has no radially outward self-bias, or is non-self-supporting, the membrane 20 is unable to maintain the lumen 22 in a fully opened/expanded configuration. In some embodiments, a similar effect may occur during insertion and advancement of the dilator 16. In some embodiments having a bulbous distal tip, vessel pressure may collapse the membrane 20 against the narrower or reduced cross-section shaft portion of the dilator 16 proximal of the bulbous distal tip as the dilator 16 is advanced through the lumen 22 of the membrane 20.

FIGS. 8 and 8A illustrate an example expandable delivery sheath 10 disposed within a vessel or body lumen 5, a medical device 18 being advanced through the lumen 22 of the membrane 20 and/or the expandable delivery sheath 10. Accordingly, the medical device 18 is shown as being advanced from a proximal end or the proximal portion of the expandable delivery sheath 10 and/or the membrane 20 toward a distal end or the distal portion of the expandable delivery sheath 10 and/or the membrane 20. The medical device 18 is schematically illustrated in FIG. 8A as a cylindrical element disposed at the distal end of an elongate shaft. One of ordinary skill in the art will recognize that the medical device 18 and the elongate shaft may be a single object, element, or device, or may be a combination of elements that together make up a medical device suitable for insertion through the expandable delivery sheath 10. For example, the medical device 18 may be a single catheter or sheath having a uniform outer diameter or the medical device 18 may be an assembly having a stepped or variable outer diameter, or the medical device 18 may be some combination of these (i.e., a single catheter with a stepped or variable outer diameter).

In some embodiments, the medical device 18 may include an atherectomy device, an angioplasty device, a balloon dilatation catheter, a distal protection device, an embolic filtering device, a valvectomy device, a valvuloplasty device, a stent delivery device, a transaortic valve implantation (TAVI) device, an ablation device, an object retrieval device, a guide catheter or sheath, a diagnostic catheter, or other suitable device. For simplicity, the following discussion will generally refer to a medical device 18, which may or may not include the elongate shaft shown in FIGS. 8-8A.

The medical device 18 may have a maximum outer diameter that may be defined as the farthest or largest radial extent from a central longitudinal axis of the medical device 18, or the maximum circumference or perimeter of the medical device 18. In some embodiments, the medical device 18 may have a maximum outer diameter of about 16 F (French, where F/3=diameter in mm), about 18 F, about 20 F, about 22 F, or more. In some embodiments, the medical device 18 may have a maximum outer diameter that is greater than the first inner diameter of the lumen 22 of the membrane 20 (i.e., the inner diameter of the lumen 22 of the membrane 20 in the delivery configuration) and/or the first outer diameter of the outer member or tear-away covering 30 (i.e., the outer diameter of the expandable delivery sheath 10 and/or the outer member or tear-away covering 30 in the delivery configuration).

Following placement within the vessel or body lumen 5, the membrane 20 may remain or be maintained in a substantially stationary position relative to the vessel or body lumen 5 as the medical device 18 is passed through the lumen 22 of the membrane 20. In other words, as the medical device 18 is advanced distally, the membrane 20 does not move axially within the vessel or body lumen 5. The membrane 20 is configured to permit the lumen 22 to radially expand around the medical device 18 as the medical device 18 is advanced through the lumen 22 of the membrane 20, as shown in FIGS. 8 and 8A. As the medical device 18 is advanced, the membrane 20 permits the medical device 18 to push the wall of the membrane 20 radially outward from a central longitudinal axis of the lumen 22 up to a second or maximum inner diameter of the lumen 22 of the membrane 20. An expandable delivery sheath 10 may be selected for use with the lumen 22 sized such that the medical device 18 is permitted to pass through the lumen 22 of the membrane 20. In some embodiments, the membrane 20 is configured to permit the lumen 22 to radially expand to a second inner diameter equal to or greater than the maximum outer diameter of the medical device 18. In some embodiments, the expandable delivery sheath 10 is configured to radially expand to a second outer diameter greater than the maximum outer diameter of the medical device 18.

FIG. 8A schematically illustrates a medical device 18 (shown in phantom) disposed within the central tapered section and/or the distal section of the expandable delivery sheath 10 and/or the membrane 20. The medical device 18 may be advanced distally through the proximal non-expandable section and as the medical device 18 reaches and/or engages the central tapered section, the medical device 18 may come into contact with an inner surface of the wall of the membrane 20 and may thereby force the outer member or tear-away covering 30 to separate, split, or tear along the plurality of openings, cutouts, perforations, notches, holes, apertures, or other weakening features formed in the wall of the outer member or tear-away covering 30, and/or may force the membrane 20 to expand around the medical device 18, in accordance with the present disclosure. In other words, in some embodiments, a medical device 18 being advanced through the delivery sheath 10 and/or the membrane 20 may cause the outer member or tear-away covering 30 to separate from the first configuration to the second configuration.

Figure 9:
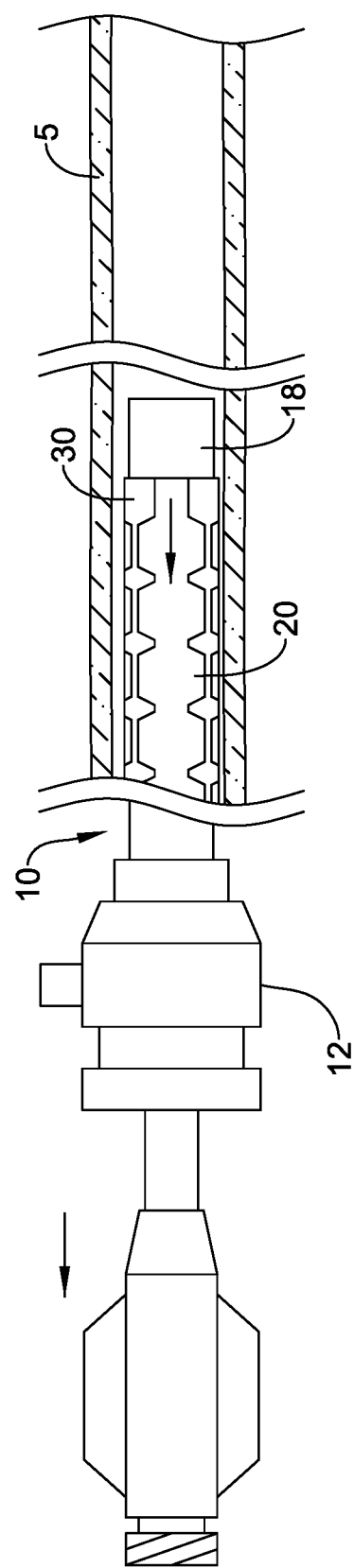
FIG. 9 illustrates an example sheath and an example medical device (or delivery device) being withdrawn from a vessel.

FIG. 9 schematically illustrates the expandable delivery sheath 10 and a medical device 18 (and/or a delivery device for a medical device left behind) being withdrawn from a patient's vessel and/or body lumen 5. In general, the expandable delivery sheath 10 and the medical device 18 may be withdrawn together, simultaneously, although in some embodiments, the medical device 18 (and/or the delivery device) may be withdrawn first and the compliant expandable delivery sheath 10 withdrawn last.

Figure 10:
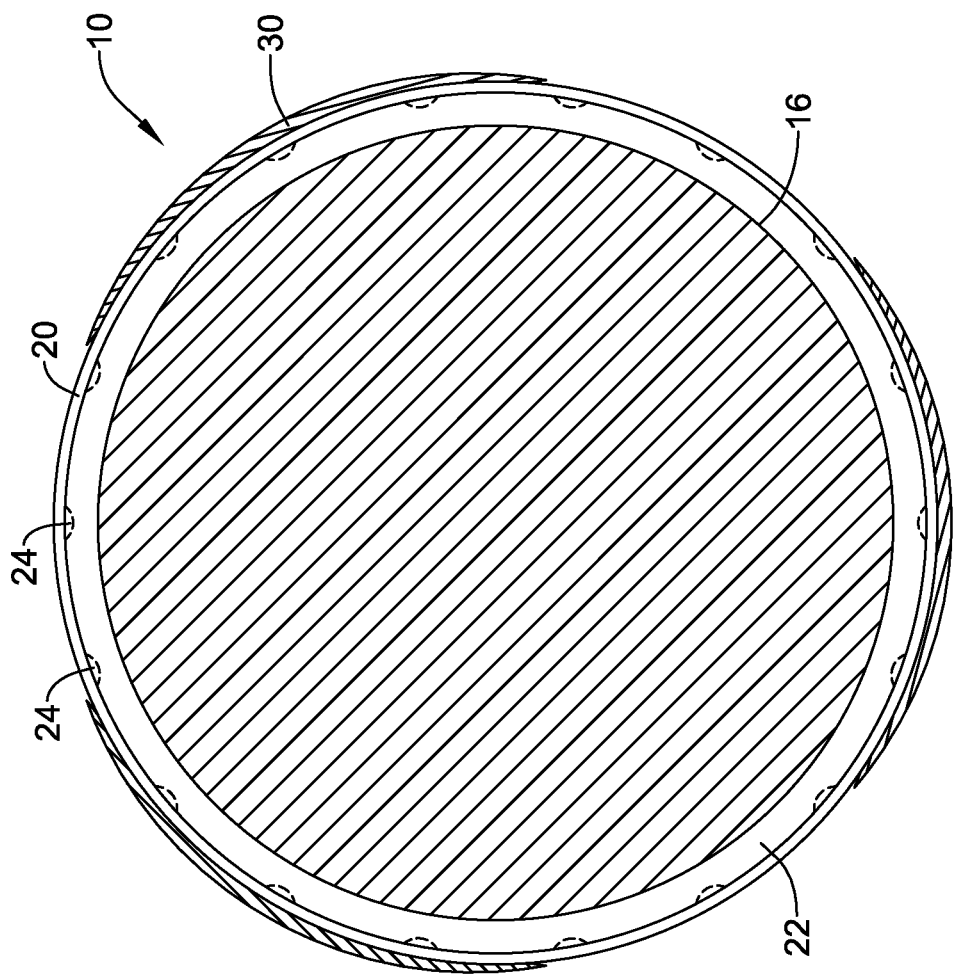
FIG. 10 is a partial cross-sectional view of an example sheath expanded by a dilator or medical device disposed therein taken along the line 10-10 of FIG. 6.

FIG. 10 illustrates a partial cross-sectional view of the expandable delivery sheath 10, including the membrane 20 and the outer member or tear-away covering 30 in the second configuration, with the dilator 16 (and/or the bulbous distal tip of the dilator 16) as in FIG. 6, disposed within the lumen 22 of the membrane 20. In some embodiments, the plurality of corrugations 24 may permit the dilator 16 to more easily slide through the lumen 22 of the membrane 20, since there is less physical, and therefore frictional, contact between the dilator 16 and the wall of the membrane 20. The plurality of corrugations 24 may contact the dilator 16 at a plurality of points or lines along its length instead of contacting over the entire outer surface of the dilator 16. Similarly, a medical device 18 may be disposed within the lumen 22 of the membrane 20, such as in FIG. 8A. A partial cross-sectional view taken through the expandable delivery sheath 10, including the membrane 20 and the outer member or tear-away covering 30 in the second configuration, with the medical device 18 disposed within the lumen 22 of the membrane 20 as in FIG. 8A, may look similar to or the same as that illustrated in FIG. 10. In some embodiments, the plurality of corrugations 24 may permit the medical device 18 to more easily slide through the lumen 22 of the membrane 20, since there is less physical, and therefore frictional, contact between the medical device 18 and the wall of the membrane 20. The plurality of corrugations 24 may contact the medical device 18 at a plurality of points or lines along its length instead of contacting over the entire outer surface of the medical device 18.

A method of manufacturing an example expandable delivery sheath 10 may include forming one or more folds in a compliant tubular membrane 20. In some embodiments, forming one or more folds in the compliant tubular membrane 20 may thereby reduce an inner diameter of the membrane 20 to a reduced inner diameter. In some embodiments, the membrane 20 may include a plurality of corrugations 24 formed along an inner surface and/or a lumen 22 thereof. In some embodiments, the method may include cutting a plurality of openings, cutouts, perforations, notches, holes, apertures, or other weakening features though a wall of a tubular outer member or covering 30 to form a tear-away covering. In some embodiments, the method may include laminating the outer member or tear-away covering 30 onto the membrane 20. In at least some embodiments, the plurality of openings, cutouts, perforations, notches, holes, apertures, or other weakening features may be disposed over the one or more folds. In some embodiments, the membrane 20 may be inelastic. In some embodiments, the outer member or tear-away covering 30 may be configured to separate along the plurality of openings, cutouts, perforations, notches, holes, apertures, or other weakening features upon passage of an apparatus, such as a dilator 16 and/or a medical device 18, having an outer diameter greater than the reduced inner diameter through the membrane 20. In some embodiments, the membrane 20 may be incapable of maintaining an increased inner diameter on its own after removal of the apparatus therefrom. In some embodiments, the method may further include, after laminating the outer member or tear-away covering 30 onto the membrane 20, attaching a proximal hub 12 to the membrane 20 and/or the outer member or tear-away covering 30, the proximal hub 12 including a port in fluid communication with a lumen 22 of the membrane 20 and a hemostatic valve or seal therein. In some embodiments, an outer surface of the membrane 20 may be conditioned (e.g., etched) to adhere to and/or bond with the outer member or tear-away covering 30.

In some embodiments, the sheath, the membrane, and/or the plurality of corrugations may be made from materials such as metals, metal alloys, polymers, ceramics, metal-polymer composites, or other suitable materials, and the like. Some examples of suitable materials may include metallic materials such as stainless steels (e.g. 304v stainless steel or 316L stainless steel), nickel-titanium alloys (e.g., nitinol, such as super elastic or linear elastic nitinol), nickel-chromium alloys, nickel-chromium-iron alloys, cobalt alloys, nickel, titanium, platinum, or alternatively, a polymeric material, such as a high performance polymer, or other suitable materials, and the like. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

In some embodiments, the sheath, the membrane, and/or the plurality of corrugations may be made from materials such as, for example, a polymeric material, a ceramic, a metal, a metal alloy, a metal-polymer composite, or the like. Examples of suitable polymers may include polyurethane, a polyether-ester such as ARNITEL® available from DSM Engineering Plastics, a polyester such as HYTREL® available from DuPont, a linear low density polyethylene such as REXELL®, a polyamide such as DURETHAN® available from Bayer or CRISTAMID® available from Elf Atochem, an elastomeric polyamide, a block polyamide/ether, a polyether block amide such as PEBA available under the trade name PEBAX®, silicones, polyethylene, Marlex high-density polyethylene, polyetheretherketone (PEEK), polyimide (PI), and polyetherimide (PEI), a liquid crystal polymer (LCP) alone or blended with other materials. In some embodiments, a suitable polymeric material may have a yield strain of at least 20%, at least 30%, at least 40%, at least 50%, or more. In some embodiments, the sheath, the membrane, and/or the plurality of corrugations may be made from a material having a low coefficient of friction. In some embodiments, the sheath, the membrane, and/or the plurality of corrugations may be formed from a fluoropolymer, such as polytetrafluoroethylene (PTFE) or fluorinated ethylene propylene (FEP).

Portions of the sheath, the membrane, and/or the medical device may be made of, may be doped with, may include a layer of, or otherwise may include a radiopaque material. Radiopaque materials are understood to be materials capable of producing a relatively bright image on a fluoroscopy screen or another imaging technique such as X-ray during a medical procedure. This relatively bright image aids the user of device in determining its location. For example, one or more of the elements described above (i.e., the sheath, the membrane, the medical device, etc.) may include or be formed from a radiopaque material. Suitable materials can include, but are not limited to, bismuth subcarbonate, iodine, gold, platinum, palladium, tantalum, tungsten or tungsten alloy, and the like.

It should be understood that although the above discussion was focused on percutaneous medical procedures within the vasculature of a patient, other embodiments or methods in accordance with the invention can be adapted and configured for use in other parts of the anatomy of a patient. For example, devices and methods in accordance with the invention can be adapted for use in the digestive or gastrointestinal tract, such as in the mouth, throat, small and large intestine, colon, rectum, and the like. For another example, devices and methods can be adapted and configured for use within the respiratory tract, such as in the mouth, nose, throat, bronchial passages, nasal passages, lungs, and the like. Similarly, the devices and methods described herein with respect to percutaneous deployment may be used in other types of surgical procedures as appropriate. For example, in some embodiments, the devices may be deployed in a non-percutaneous procedure. Devices and methods in accordance with the invention can also be adapted and configured for other uses within the anatomy.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed:

1. A method of manufacturing an expandable sheath, comprising:
    forming a compliant tubular membrane with a plurality of longitudinal corrugations extending radially inward from an inner surface of the compliant tubular membrane, the compliant tubular membrane having an inner diameter;
    forming a plurality of longitudinally oriented folds in the compliant tubular membrane, thereby reducing the inner diameter of the compliant tubular membrane to a reduced inner diameter, wherein at least some of the plurality of longitudinal corrugations extend radially inward from the plurality of longitudinally oriented folds;
    forming a plurality of apertures through a wall of a tubular outer covering; and
    laminating the tubular outer covering onto the compliant tubular membrane, wherein the plurality of apertures is disposed over the plurality of longitudinally oriented folds.

2. The method of claim 1, wherein the plurality of longitudinal corrugations is arranged angularly equidistantly around a central longitudinal axis of the compliant tubular membrane.

3. The method of claim 1, wherein the plurality of longitudinal corrugations each define a convex shape extending radially inwardly from the inner surface of the compliant tubular membrane.

4. The method of claim 1, wherein the plurality of longitudinal corrugations is formed with a height from the inner surface of the compliant tubular membrane to an innermost radial extent of the plurality of longitudinal corrugations that is less than a thickness of a wall of the compliant tubular membrane.

5. The method of claim 4, wherein the height is about 50% of the thickness of the wall of the compliant tubular membrane.

6. The method of claim 4, wherein the height is about 75% of the thickness of the wall of the compliant tubular membrane.

7. The method of claim 4, wherein the height is about 95% of the thickness of the wall of the compliant tubular membrane.

8. The method of claim 1, wherein the tubular outer covering is configured to separate along the plurality of apertures upon passage of an apparatus having an outer diameter greater than the reduced inner diameter through the compliant tubular membrane.

9. A method of manufacturing an expandable sheath, comprising:
    forming a plurality of longitudinally oriented folds in a compliant tubular membrane, thereby reducing an inner diameter of the compliant tubular membrane to a reduced inner diameter;
    wherein after forming the plurality of longitudinally oriented folds, a plurality of longitudinally oriented corrugations extends radially inward from a radially inwardly facing surface of the compliant tubular membrane, the plurality of longitudinally oriented corrugations being arranged angularly equidistantly around a central longitudinal axis of the compliant tubular membrane;
    forming a plurality of apertures through a wall of a tubular outer covering; and
    laminating the tubular outer covering onto the compliant tubular membrane, wherein the plurality of apertures is disposed over the plurality of longitudinally oriented folds.

10. The method of claim 9, wherein at least some of the plurality of longitudinal corrugations extend radially inward from the plurality of longitudinally oriented folds.

11. The method of claim 9, wherein at least one of the plurality of longitudinal corrugations extends radially inward from a radially innermost longitudinally oriented fold of the plurality of longitudinally oriented folds.

12. The method of claim 9, wherein at least some longitudinally oriented folds of the plurality of longitudinally oriented folds overlap in a radial direction relative to the central longitudinal axis.

* * * * *